(12) United States Patent
Lorge

(10) Patent No.: US 10,519,553 B2
(45) Date of Patent: Dec. 31, 2019

(54) METHOD FOR DISSOCIATING WATER USING PHOTOSYSTEM II (PSII)

(71) Applicant: H2WIN S.A., Nivelles (BE)

(72) Inventor: Philippe Lorge, Nivelles (BE)

(73) Assignee: H2WIN S.A., Nivelles (BE)

( * ) Notice: Subject to any disclaimer, the term of this patent is extended or adjusted under 35 U.S.C. 154(b) by 778 days.

(21) Appl. No.: 15/021,579

(22) PCT Filed: Sep. 11, 2014

(86) PCT No.: PCT/EP2014/069418
§ 371 (c)(1),
(2) Date: Mar. 11, 2016

(87) PCT Pub. No.: WO2015/036496
PCT Pub. Date: Mar. 19, 2015

(65) Prior Publication Data
US 2016/0230292 A1    Aug. 11, 2016

(30) Foreign Application Priority Data
Sep. 11, 2013    (BE) .................................... 2013/0598

(51) Int. Cl.
*C25B 1/00*    (2006.01)
*C01B 3/04*    (2006.01)
(Continued)

(52) U.S. Cl.
CPC .............. *C25B 1/003* (2013.01); *C01B 3/042* (2013.01); *C01B 13/0207* (2013.01); *C12P 3/00* (2013.01);
(Continued)

(58) Field of Classification Search
CPC . C25B 1/003; C25B 1/04; H01M 8/16; C01B 3/042; C01B 13/0207; C12P 3/00; Y02E 60/366; Y02E 60/364; Y02P 20/134
(Continued)

(56) References Cited

U.S. PATENT DOCUMENTS

2006/0166343 A1*  7/2006  Hankamer ............... C12N 1/12
                                                 435/168
2009/0155875 A1*  6/2009  Berry .................... C12N 9/0008
                                                 435/168
(Continued)

FOREIGN PATENT DOCUMENTS

EP    1 134 585 A2    9/2001

OTHER PUBLICATIONS

Bittner et al, "Nonlinear Laserspectroscopic Investigations of the Pigment-Pigment Interaction Within the Light-Harvesting Complex of Photosystem II," Photochemistry and Photobiology, vol. 57, No. 1, pp. 158-162, 1993 (Year: 1993).*
(Continued)

*Primary Examiner* — Nicholas A Smith
*Assistant Examiner* — Colleen M Raphael
(74) *Attorney, Agent, or Firm* — Christensen O'Connor Johnson Kindness PLLC

(57) ABSTRACT

The invention relates to a method for dissociating an aqueous solution which includes electrochemical oxidation of the aqueous solution in the presence of pulsed light, said pulsed light being generated from a first source of light energy with a predetermined pulse frequency value, using an enzyme composition based on a first enzyme complex PSII, isolated from a second enzyme complex PSI, with production of oxygen, free electrons and free protons in the aqueous solution, characterised in that said light energy has a variable energy value over time, said method also including a step of
(Continued)

Extraction of PSII: Fluorescence Spectrum modulating said predetermined pulse frequency value of said pulsed light.

9 Claims, 6 Drawing Sheets

(51) Int. Cl.
    *C01B 13/02* (2006.01)
    *C12P 3/00* (2006.01)
    *C25B 1/04* (2006.01)
    *H01M 8/16* (2006.01)

(52) U.S. Cl.
    CPC ............. *C25B 1/04* (2013.01); *H01M 8/16* (2013.01); *Y02E 60/364* (2013.01); *Y02E 60/366* (2013.01); *Y02P 20/134* (2015.11)

(58) Field of Classification Search
    USPC .......................................... 205/340; 204/248
    See application file for complete search history.

(56) References Cited

U.S. PATENT DOCUMENTS

2010/0200049 A1    8/2010    Kufryk et al.
2016/0193595 A1*    7/2016    Nagpal .................... C25B 3/04
    502/215

OTHER PUBLICATIONS

Jursinic, P., et al., "Enhanced Oxygen Yields Caused by Double Turnovers of Photosystem II Induced by Dichlorobenzoquinone," Biochimica et Biophysica Acta 934(2):177-185, Jul. 6, 1988.

Shevela, D., et al., "Probing the Turnover Efficiency of Photosystem II Membrane Fragments With Different Electron Acceptors," Biochimica et Biophysica Acta 1817(8):1208-1212, Mar. 29, 2012.

International Search Report dated Dec. 9, 2014, issued in corresponding International Application No. PCT/EP2014/069418, filed Sep. 11, 2014, 3 pages.

Written Opinion of the International Searching Authority, issued in corresponding International Application No. PCT/EP2014/069418, filed Sep. 11, 2014, 10 pages.

Written Opinion of the International Searching Authority dated Dec. 9, 2014, issued in corresponding International Application No. PCT/EP2014/069418, filed Sep. 11, 2014, 11 pages.

International Preliminary Report on Patentability dated Mar. 15, 2016, issued in corresponding International Application No. PCT/EP2014/069418, filed Sep. 11, 2014, 1 page.

\* cited by examiner

METHOD FOR DISSOCIATING WATER USING PHOTOSYSTEM II (PSII)

FIELD OF THE DISCLOSURE

Embodiments of the present disclosure relate to a method for dissociating an aqueous solution comprising:

a first electrochemical oxidation of the aqueous solution in the presence of pulsed light, which pulsed light is generated from a first source of light energy at a predetermined pulse frequency value, by an enzymatic composition based on a first enzymatic complex PSII, isolated from a second enzymatic complex PSI, with production of oxygen, free electrons and free protons in the aqueous solution, a capture of the free electrons and the free protons, and a separate oxygen capture.

Optionally, the pulsed light is a coherent light, i.e. generated by a laser.

Such a method is for example known from document *Biochimica et Biophysica Acta* 1817 (2012) 1028-1212, of Sheleva and Messinger, which discloses the electrochemical oxidation of water in the presence of light.

BACKGROUND

This method most particularly finds its application within the scope of producing renewable energy from solar light.

PSII is a photosensitive enzymatic molecular complex comprising pigments (chlorophyll) which is the centre of water hydrolysis in the chloroplasts present in the cytoplasm of plant cells according to the following reaction:

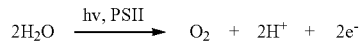

$$2H_2O \xrightarrow{h\nu, PSII} O_2 + 2H^+ + 2e^-$$

wherein hv corresponds to a light photon, for example of solar light, $H_2O$ is water, H+ represents a free proton and e represents a free electron.

The enzymatic complex PSII, because of its hydrolyzing function, produces from light, oxygen on the one hand, and free electrons and free protons on the other hand, is of a particular interest within the scope of its use for producing, via a cathode, a clean fuel which is hydrogen gas (as a gas under standard temperature and pressure conditions). Indeed, the cathode gives the possibility of recombining the $e^-$ and the $H^+$ (reduction reaction of protons) in order to form the hydrogen. With this in mind, this enzymatic complex is a promising actor for producing clean fuel, i.e. the combustion of which is not associated with the production of $CO_2$, from natural energy: light, which furthermore is a quasi-inexhaustible source of energy.

Consequently, hydrogen gas, resulting from the reduction of the free protons which are associated with the free electrons, combines to oxygen resulting from the hydrolysis reaction in order to produce a combustion reaction, which results in production of energy on the one hand and of water on the other hand which may be again hydrolyzed by the PSII complex, so that a water cycle is formed, thereby forming a quasi-inexhaustible source of clean fuel. Further, the oxidation assisted by the PSII complex allows the formation of oxygen and hydrogen in situ, and is an answer to the present problematical question of the conditioning of hydrogen which, when it is formed in situ, no longer requires being stored under limiting packaging forms such as those known presently: large volumes, significant pressures, etc.

According to the document *Biochimica et Biophysica Acta* 1817 (2012) 1028-1212, there are successive absorptions of photons of light by the pigments of PSII. To each absorption corresponds a chemical oxidation-reduction reaction which takes place in the enzymatic complex PSII. Moreover it is known from the state of the art that the successive absorption of four light photons by the pigments of PSII exclusively allows successive achievement of four oxidation-reduction reactions forming a photochemical cycle (Kok cycle) at the origin of the oxidation of water into oxygen, on the one hand, and into free protons and free electrons on the other hand.

Moreover, it is known from the state of the art that the activity of the PSII complex is inter alia regulated by that of the PSI complex.

The activity of PSII is measured by the production rate of oxygen in the water, the higher this rate, the higher is the yield of the water oxidation reaction by PSII, i.e. the higher is the amount of produced oxygen.

Indeed it is known that, the presence of the PSI complex, because of its function in the mechanism for producing energy by photosynthesis, consumes the free photons and electrons indirectly intended subsequently for the reaction of synthesis of sugars by polymerization of $CO_2$.

It is therefore advantageous that the PSII complex is insulated from the PSI complex so that the water oxidation reaction increases in yield. In practice, the PSII complex is isolated from the PSI system, the latter being replaced by a sensor (device, product, material) or a group of electron and proton sensors which have the property of not inhibiting the activity of PSII. As an example, the electron and proton sensor may also be a cathode allowing reduction of the protons into hydrogen gas.

By the term of «isolated» is meant in the sense of the disclosure that the PSI complex is not able to cooperate with the enzymatic complex PSII.

In the aforementioned method, the activity of the PSII is mainly limited by the concentration and the nature of the electron sensors and proton sensors or electron and proton sensors which, for example react with the free protons and the free electrons in order to undergo reduction.

This aspect is moreover underlined in the article of Sheleva and Messinger mentioned at the beginning and wherein the authors demonstrate the efficiency of the turnovers for an enzymatic complex PSII according to the chemical nature of the electron sensors.

By the term of «turnovers» should be understood the number of steps of each looped Kok cycle per unit time, it being understood that a full Kok cycle comprises four successive turnovers since it is associated with consecutive absorption of four protons of light.

During the interaction of light with the enzymatic complex, a first charge separation $S_0 \rightarrow S_1$ takes place and is followed by three other charge separations $S_1 \rightarrow S_2$, $S_2 \rightarrow S_3$, and $S_3 \rightarrow S_4$. With each of these charge separations is associated an oxidation-reduction reaction of the Kok cycle with, when the cycle is a closed loop, formation of oxygen and of free protons as well as free electrons, and the return of the complex from the state $S_4$ to the state $S_0$.

In particular, the authors demonstrate that one of the four oxidation-reduction reactions of the Kok cycle: the reduction reaction, governed by the reactivity of the electron sensor, is the limiting step of the Kok cycle.

Also, Sheleva and Messinger suggest that the yield of the enzymatic complex PSII may be optimized by selecting a predetermined pulse frequency value which is a specific pulse frequency of the pulsed light associated with a predetermined reduction reaction rate which occurs in the immediate environment of the electron capture group of the enzymatic complex PSII.

In this way, to a specific electron sensor corresponds a specific pulse frequency: the question is therefore to optimize the pulsed frequency of the pulsed light according to the reduction reaction rate on the reducing site of the enzymatic complex PSII and therefore according to the chemical nature of the electron sensor in order to have a number of turnovers per unit time as high as possible, and therefore of the number of Kok cycles per unit time.

Unfortunately, if the method of the state of the art puts forward promising conclusions as regards an optimization route of the operation of the enzymatic complex PSII, it remains nevertheless limited to a major constraint in the requirement of having a source of light of constant energy in time and sufficient for saturating the Kok cycle of the enzymatic complex PSII, the energy level of the light source being governed by the physicochemical nature of the enzymatic complex PSII, in particular by the chemical composition of the electron capture and donor groups.

SUMMARY

The object of the disclosure is to overcome this drawback of the state of the art by providing a cost-effective method for dissociating an aqueous solution, while allowing the utilization on an industrial scale of a source of light energy and uncontrolled, such as for example solar energy or electric energy of a renewable origin, and transforming it into hydrogen and oxygen produced in situ so as to be able to have a source of fuel and a source of oxidizer which may be directly used for example on site.

In order to solve this problem, a method as indicated initially is provided, wherein the light energy has a variable energy value overtime and wherein the method further comprises a step for modulating the predetermined pulse frequency value of the pulsed light to a sufficient pulse frequency value in order to obtain a first yield for producing oxygen per unit of light energy which is greater by a factor comprised between 1.01 and 100.00 than a second oxygen production yield per light energy unit obtained for a second electrochemical oxidation in the presence of continuous light, the pulsed lights and continuous lights have an equal predetermined wavelength and an equal predetermined power.

Thus, with the method according to the present disclosure, for irradiation of the enzymatic complex PSII at the sufficient pulse frequency value, the production of oxygen and hydrogen is easily ensured which, as compared with an application of the method in the presence of a continuous light with equal power, is characterized by a surprisingly much higher yield.

Indeed, although this phenomenon is not yet well understood, it was observed in a quite surprising way that by modulating the amount of variable light energy overtime in the form of pulsed light energy at a pulsed frequency having the sufficient pulse frequency value, the oxygen production rate during the oxidation of water and therefore the activity of the PSII are increased for a given incident total energy value, as demonstrated in the examples of the present application.

A contrario, Sheleva and Messinger, which use different predetermined pulse frequency values for stimulating the enzymatic complex, however have to ensure that a predetermined and constant number of pulses are generated and that each pulse has the same energy, so that the total energy provided to the system is constant overtime. Also, for a predetermined pulse frequency, one skilled in the art who would like to apply this method should then make sure that the enzymatic complex has been well irradiated with the predetermined number of pulses and should therefore adjust the irradiation duration according to the selected pulse frequency in order to ensure a constant incident total energy value.

This aspect of the method of the state of the art is most particularly a constraint as soon as the question is to set into place industrially this method of the state of the art for example, by benefiting from the light of the sun for producing hydrogen and oxygen.

As an illustration, in the example of Table 2 shown in the results relative to the present disclosure, the maximum oxygen production rate per unit energy measured in the presence of pulsed light is at least 20 times higher than the rate measured during the application of the water hydrolysis method in the presence of continuous light, and this for a same predetermined light power value set to 555 mW.

Indeed, within the scope of the present disclosure, it was observed that for a sufficiently intense and short pulse (so as to be able to saturate the Kok cycle by providing it with the sufficient minimum energy for the activity to induce electrochemical dissociation of water), a first charge separation ($S_0 \rightarrow S_1$) takes place in the enzymatic complex, the number of first charge separations is governed by the sufficient pulsed frequency value of the pulsed light.

The selection of the sufficient pulse frequency value is determined by: (i) the light absorption profile of the enzymatic complex and therefore by the wavelength of the pulsed light; (ii) as well as by the energy value of the energy of the incident light.

Also, when the energy value of the light energy is higher, the sufficient pulse frequency value is higher, conversely, when the energy value of the light energy is smaller, the sufficient pulse frequency value is smaller.

Thus, the number of pulses varies so that the energy value of each pulse is sufficient for generating the first charge separation ($S_0 \rightarrow S_1$) in the enzymatic complex. The energy value of each pulse depends on the energy value of the light energy and on the selection of the sufficient pulse frequency value for obtaining the claimed oxygen production yield per light energy unit.

The method according to the disclosure therefore is an alternative to a simpler application than that of the method disclosed in the state of the art since it does not require both control of the energy applied to the system and the pulse frequency with which this energy is applied but only of the pulse frequency of the pulsed light.

Advantageously, before the electrochemical oxidation step of the aqueous solution, the method comprises a step for extracting the enzymatic complex PSII from chloroplasts or tylakoids of chloroplasts.

In a particular embodiment, the method comprises, after the step for extracting the PSII, a step for purifying the enzymatic complex PSII in order to form an enzymatic composition substantially concentrated with PSII.

Preferably, the chloroplasts or tylakoids of chloroplasts are chloroplasts or tylakoids of chloroplasts of plants from the family of Chenopodiaceae, preferably of the genus *Spinacia* and from the family of Characeae, preferably prokaryotic or eukaryotic algae.

Alternatively, the PSII complex is a synthesis complex resulting from a step for synthetically manufacturing the enzymatic complex PSII, the manufacturing step being carried out prior to the oxidation step of the aqueous solution.

In a particularly advantageous embodiment of the method, the capture of free electrons and of free protons is carried out by an electron transport mediator selected for example from the group consisting of derivatives of quinone, preferably from among 2,6-dimethylbenzoquinone, 2,6-dichloro-p-benzoquinone and 1,4-benzoquinone, or one of their mixtures.

Optionally, the pulsed light is emitted at a pulse frequency comprised between 1 Hz and 100 MHz, preferably comprised between 1 Hz and 3,000 Hz, in a range of wavelengths comprised between 400 nm and 700 nm, preferably between 500 nm and 680 nm, at a power comprised between 1 mW and 800 mW, preferably between 500 and 700 mW.

In a particular embodiment, the method is characterized in that the water oxidation is carried out at a pH comprised between 4 and 8, preferably between 6 and 7.

The application of the method in a pH range comprised between 6 and 7 ensures optimum enzymatic activity of the PSII complex.

Other embodiments of the method are indicated in the appended claims.

The object of the disclosure is also a use of pulsed light, which pulsed light generated from a first source of light energy at a predetermined pulsed frequency value, for producing electrochemical oxidation of water in the presence of light by means of a photosensitive biochemical system comprising:

an enzymatic composition based on a first enzymatic complex PSII, isolated from a second enzymatic complex PSI, laid out so as to oxidize water into oxygen and for releasing together free electrons and free protons in the water, a first sensor of the free electrons and a second sensor of the free protons, or a third sensor of the free electrons and the free protons, which may for example be a cathode, and a fourth oxygen sensor which may for example be a container for storing oxygen, wherein the light energy has a variable energy value overtime and wherein the predetermined pulse frequency value of the pulse light is modulated at a sufficient pulse frequency value in order to obtain a first oxygen production yield per light energy unit which is greater by a factor comprised between 1.01 and 100.00 than a second oxygen production yield per light energy unit obtained for a second electrochemical oxidation in the presence of continuous light, the pulsed lights and continuous lights having an equal predetermined wavelength and an equal predetermined power.

Advantageously, the enzymatic complex PSII is extracted from chloroplasts or tylakoids of chloroplasts Preferably, the enzymatic complex PSII is purified in order to form an enzymatic composition substantially concentrated with PSII.

In a preferential method of use, the chloroplasts or tylakoids of chloroplasts are chloroplasts or tylakoids of chloroplasts of plants from the family of Chenopodiaceae, preferably of the genus *Spinacia* or from the family of Characeae, preferably prokaryotic or eukaryotic algae.

In particular, the enzymatic complex PSII is a synthetic enzymatic complex.

Alternatively, the sensor of free electrons and of free protons is an electron transport mediator selected from the group for example consisting of derivatives of quinone, preferably from among 2,6-dimethylbenzoquinone, 2,6-dichloro-p-benzoquinone and 1,4-benzoquinone, or one of their mixtures.

Particularly, the mediator is present in the water at a concentration comprising 1 µM and 1 M. Preferably, the PSII is deposited on a substrate. The PSII concentration in this scenario at least greater than 1 M, the substrate playing then the role of an anode, centre of the oxidation of the water contained in the aqueous solution.

Preferably, the mediator is present in the water at a concentration comprised between 10 µM and 1 mM and wherein the PSII is present in the water at a concentration comprised between 1 µg Chl/ml and 1 g Chl/ml, preferably between 20 µg Chl/ml and 200 µg Chl/ml. In the sense of the disclosure, the PSII concentrations are traditionally expressed relatively to the total chlorophyll concentration (Chl). By total chlorophyll concentration should be understood in the sense of the disclosure the concentration of A and B chlorophylls.

Preferentially, the pulsed light is emitted at a pulse frequency comprised between 1 Hz and 100 MHz, preferably comprised between 1 Hz and 3,000 Hz, in a range of wavelengths comprised between 400 nm and 700 nm, preferably between 500 nm and 680 nm, at a power comprised between 1 mW and 800 mW, preferably between 500 and 700 mW.

Advantageously, the use of pulsed light according to the disclosure is characterized in that the water oxidation is carried out at a pH comprised between 4 and 8, preferably between 6 and 7.

Other embodiments of the use of the pulsed light are indicated in the appended claims.

Embodiments of the present disclosure also relate to a device for applying the method according to the disclosure, the device comprising:

a source of light energy intended to produce pulsed light for which the light energy has a variable energy value overtime;

a modulator of the pulse frequency of the pulsed light;

a reactor for dissociating an aqueous solution comprising an aqueous phase, which reactor is laid out so that the solution may be irradiated with the pulsed light when the latter is generated;

an enzymatic composition in solution in the aqueous phase, which enzymatic composition comprises a first complex PSII, isolated from a second enzymatic complex PSI, which enzymatic composition is laid out so that, under the action of the pulsed light, electrochemically oxidizing the aqueous solution for producing oxygen, free electrons and free protons in the aqueous solution;

a first means for capturing oxygen;

a second means for capturing free electrons and free protons.

Other embodiments of the device according to the disclosure are indicated in the appended claims.

DESCRIPTION OF THE DRAWINGS

The foregoing aspects and many of the attendant advantages of the claimed subject matter will become more readily appreciated as the same become better understood by reference to the following detailed description, when taken in conjunction with the accompanying drawings, wherein:

DETAILED DESCRIPTION

Figure 1:
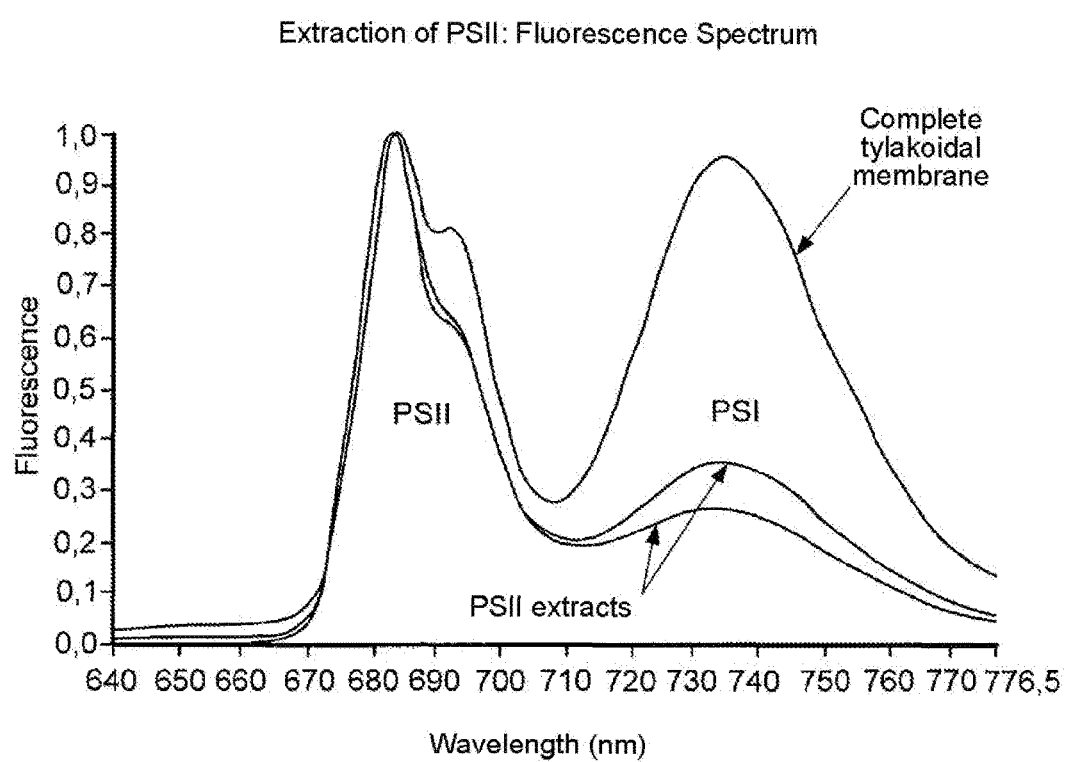
FIG. 1 illustrates the absorption spectra of PSII before and after purification according to a method for extracting the complex PSII from chloroplasts of spinach.

The detailed description set forth below in connection with the appended drawings, where like numerals reference like elements, is intended as a description of various embodiments of the disclosed subject matter and is not intended to represent the only embodiments. Each embodiment described in this disclosure is provided merely as an example or illustration and should not be construed as preferred or advantageous over other embodiments. The illustrative examples provided herein are not intended to be exhaustive or to limit the claimed subject matter to the precise forms disclosed.

The device used for applying the method according to the present disclosure, for which the performances are illustrated in the following examples, comprises:

a source of light energy intended to produce a pulsed light for which the light energy has a variable energy value over time;

a modulator of the pulse frequency of the pulsed light;

a reactor for dissociating an aqueous solution comprising an aqueous phase, which reactor is laid out so that the solution may be irradiated with the pulsed light when the latter is generated;

an enzymatic composition in solution in the aqueous phase, the enzymatic composition comprises a first complex PSII, isolated from a second enzymatic complex PSI, the enzymatic composition is laid out for, under the action of the pulsed light, electrochemically oxidizing the aqueous solution in order to produce oxygen, free electrons and free protons in the aqueous solution;

a first means for capturing oxygen;

a second means for capturing free electrons and free protons.

During operation, the pulsed light is generated at a first predetermined pulse frequency and the pulsed light source is oriented so that the pulsed light irradiates the photo-enzymes in the aqueous solution.

The irradiation of the enzymatic complex in suspension in the solution induces an oxidation reaction of the water contained in the reactor via the PSII enzymatic complex with production of oxygen which is captured by the first capture means which is for example an electrode of the Clark type immersed in the aqueous phase, the free electrons and the free protons are as for them captured by the second capture means which is a sensor of electrons, for example dimethylbenzoquinone (DMBQ) or 2,5-dichloro-p-benzoquinone (DCBQ).

As the energy value of the light energy varies over time, the modulator of the pulse frequency of the pulsed light, which pulsed light is associated with this variable light energy, gives the possibility when it operates of modulating the predetermined pulse frequency value of this pulsed light at a sufficient pulse frequency value for obtaining a first oxygen production yield per unit of light energy which is greater by a factor comprised between 1.01 and 100.00 at a second oxygen production yield per unit of light energy obtained for a second electrochemical oxidation in the presence of continuous light, which pulsed light and continuous lights have an equal predetermined wavelength and an equal predetermined power.

Preferably, the first oxygen production yield per unit of light energy which is greater by a factor comprised between 1.01 and 80.00 than a second oxygen production yield per unit of light energy obtained for a second electrochemical oxidation in the presence of continuous light, which pulsed lights and continuous lights have an equal predetermined wavelength and an equal predetermined power.

By the terms of «pulse frequency», should be understood in the present disclosure the frequency with which is modulated the energy value of the light energy emitted at a predetermined wavelength or in a predetermined range of wavelengths.

Example 1: Preparation of the Enzymatic Composition Based on PSII

As mentioned earlier, the PSI complex which inhibits the activity of the PSII complex and which therefore limits the formation of oxygen should be removed.

Chloroplasts from spinach (*Spinacia oleracea*) are extracted in accordance with the procedure developed by Barthelemy et al. (Journal of Photochemistry and Photobiology B: Biology, 1997, volume 39, pages 213-218), and then extracted from thylakoid membranes and dissociated from the PSI complex present in these membranes, the PSII complex according to the method of Berthold and al., see Febs Letters, 1981, volume 134, number 2, pages 231-234.

As compared with the Barthelemy procedure, in the method according to the disclosure, mention is made of the following modifications:

the absolute concentration of Triton® X 100 is maintained constant in the sample of an aqueous solution by adjusting the chlorophyll concentration to 200 µg/ml before adding 25 mg of Triton® X 100 for 1 mg of chlorophyll to the sample, and the second treatment with Triton® X 100 is excluded and replaced by rinsing of the PSII particles in an MES-NaOH 20 mM buffer (comprising 15 mM NaCl and 5 mM $MgCl_2$) at pH=6.5 and a suspension of these particles in an MES- NaOH 20 mM buffer (comprising 15 mM NaCl, 5 mM MgCl$_2$, 0.5 M sucrose) at pH=6.5.

The PSII obtained by the modified Bertold and al. method, as described above is then kept at −80° C. after freezing in liquid nitrogen at a temperature of −196° C. (77K) for a period of 10 s.

According to the modified extraction method described above, the PSII of the spinach is isolated from the PSI complex present in the chloroplast. Indeed, as shown by FIG. 1, the absorption peak appearing at 735 nm corresponds to that of the PSI complex while the absorption peak at 685 nm corresponds to the PSII complex, this peak decreasing the energy value by a factor 5 after purification according to the method of the present example, which corresponds to a decrease by a factor 5 of the PSI concentration.

Comparative Example 1: Measurement of the Maximum Oxygen Production Rate with the PSII Complex in Continuous Light and in Monochromatic Pulsed Light at 673 nm A photohydrolysis system consisting of a cell, with a volume of 2.5 ml, the walls of which are provided with glass windows, in which a PSII suspension is placed in an aqueous solution at a buffer pH of 6.5, containing dimethylbenzoquinone (DMBQ) or 2.5-dichloro-p-benzoquinone (DCBQ).

The cell is illuminated with a laser light beam at 673 nm, in a continuous mode or in a pulsed mode. The characteristics of the laser are repeated in Tables 1a (DMBQ) and 1b (DCBQ).

By the terms of «pulsed light» or «pulsed mode» is meant in the sense of the disclosure an intermittent light, i.e. for which the energy value alternately assumes a first zero value and a second non-zero predetermined value at a predetermined pulse frequency, for example 800 Hz, which means that the energy value passes 800 times per second from the zero value to the predetermined non-zero value by the power of the light.

TABLE 1a

Characteristics of the laser used for the PSII-DMBQ system

| Parameters | Specifications |
| --- | --- |
| Type of laser | VCSEL |
| Laser emission wavelengths | 671 nm at 15° C. |
|  | 676 nm at 35° C. |
| Spectral width | <2 nm FWHM |
| Operating mode | continuous or pulsed |
| Average power | 550 mW (continuous and pulsed mode) |
| Peak power | >700 mW (pulsed mode) |
| Repetition rate | from 1 Hz to 3,000 Hz (pulsed mode) |
| Pulse duration | 9.2 μs (pulsed mode) |
| Optical output | collimated, linear, or focused |

TABLE 1b

Characteristics of the laser used for the PSII-DCBQ system

| Parameters | Specifications |
| --- | --- |
| Type of laser | VCSEL |
| Laser emission wavelengths | 671 nm at 15° C. |
|  | 676 nm at 35° C. |
| Spectral width | <2 nm FWHM |
| Operating mode | continuous or pulsed |
| Average power | 642 mW (continuous and pulsed mode) |
| Peak power | 555 mW (pulsed mode) |

TABLE 1b-continued

Characteristics of the laser used for the PSII-DCBQ system

| Parameters | Specifications |
| --- | --- |
| Repetition rate | from 1 Hz to 5,000 Hz (pulsed mode) |
| Pulse duration | 1.5 μs (pulsed mode) |
| Optical output | collimated, linear, or focused |

The rate of the increase in oxygen concentration under illumination was measured at 25° C. by using an electrode of the Clark type in an aqueous buffer solution with a concentration of 25 mM MES-NaOH (pH=6.5) and 1 mM of DMBQ.

Figure 2:
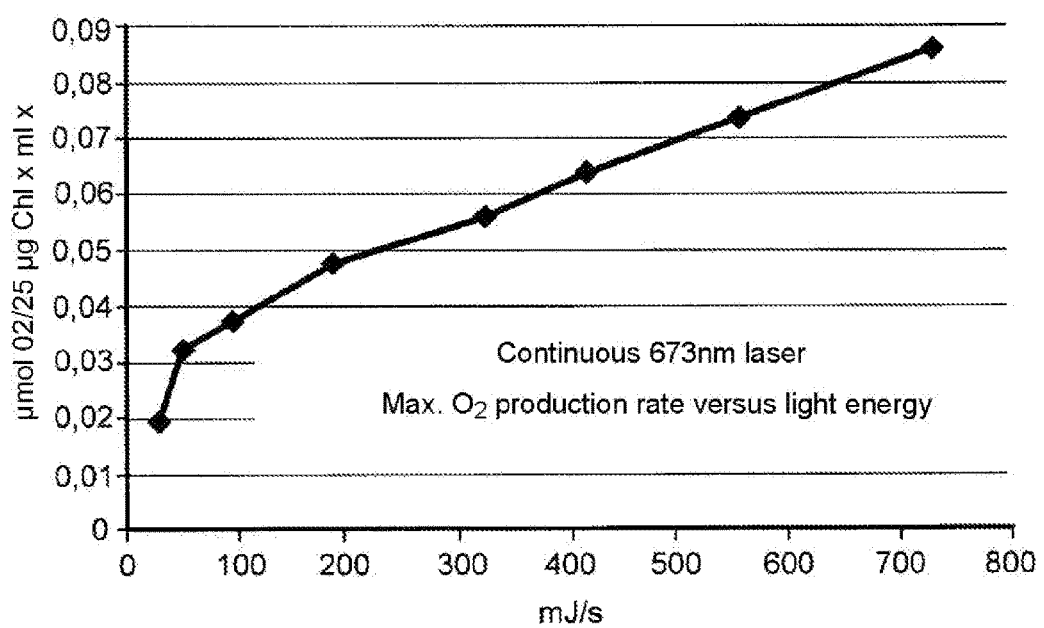
FIG. 2 illustrates a curve of the time-dependent change in the maximum oxygen production rate obtained by the method in the presence of continuous coherent light of a wavelength of 673 nm, versus the light energy value per second.

FIG. 2 illustrates a curve of the time-dependent change in the maximum oxygen production rate (in moles) for 25 μg of chlorophyll (Chl), treated with the method according to example 1, per ml of aqueous solution and per minute (min). The curve is obtained in the presence of continuous coherent light with a wavelength of 673 nm, versus the value of the light energy per second (in mJ/sec).

Figure 3:
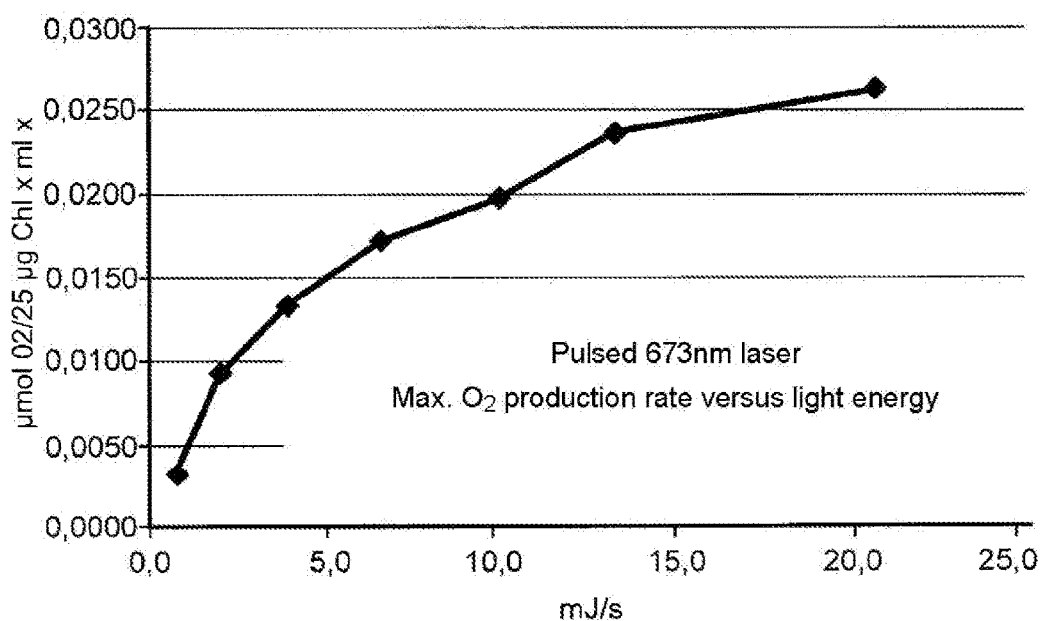
FIG. 3 illustrates a curve of the time-dependent change of the maximum oxygen production rate obtained by the method in the presence of pulsed coherent light at 800 Hz (pulses with a duration of 9.2 µs) with a wavelength of 673 nm, versus the value of the light energy per second.

FIG. 3 illustrates a curve of the time-dependent change in the maximum oxygen production rate (in moles) for 25 μg of chlorophyll (Chl), treated by the method according to example 1, per ml of aqueous solution and per minute (min). The curve is obtained in the presence of pulsed coherent light at 800 Hz with a wavelength of 673 nm, versus the value of the light energy per second (in mJ/sec).

The analysis of FIGS. 2 and 3 gives the possibility of observing, for example, that having available a light power of 500 mW, the amount of energy per second in continuous light is equivalent to 500 mJ/s. To this amount of energy in continuous light corresponds an oxygen production rate $K(O_2)$ of $7 \cdot 10^{-2}$ moles/(25 μg Chl ml min).

In the presence of pulsed light, at a power of 500 mW, emitted at a pulse frequency of 100 Hz, i.e. an energy of 5 mJ/s, corresponds an oxygen production rate $K(O_2)$ (per energy) of 0.01535 μmoles/(25 μg Chl ml min) per 500 mJ/s, i.e. an increase by a factor 21.9 of the energy yield, as compared with the rate measured in the presence of continuous light. The results of the experimental confirmation of this analysis are repeated in Table 2 below.

TABLE 2 comparison of the oxygen production rate in the presence of pulsed or continuous light, with a power of 555 mW at 673 nm.

| Mode | Energy/s mJ/s | $K(O_2)$ μmol/(25 μg Chl ml min) | Yield [$K(O_2)$/energy unit]* |
| --- | --- | --- | --- |
| Continuous | 555 | 0.0846 | $1.52 \cdot 10^{-4}$ |
| Pulsed | 5.4 | 0.0174 | $32.22 \cdot 10^{-4}$ |

*μmol/(25 μg Chl ml min mJ)

Figure 4:
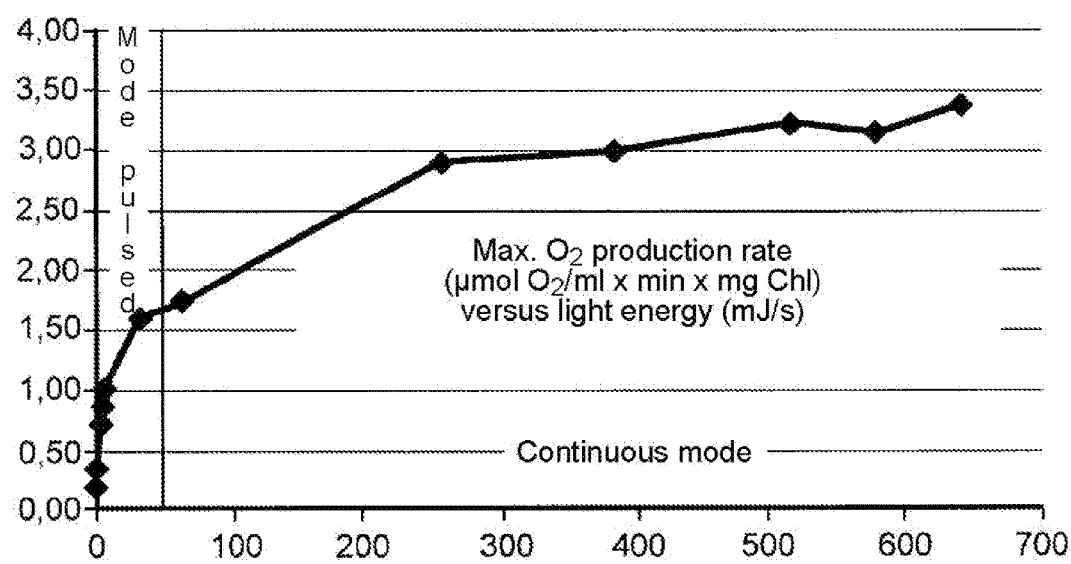
FIG. 4 illustrates the curves of the time-dependent change of the maximum oxygen production rate obtained by the method in the presence of continuous coherent light, or of pulsed coherent light at 800 Hz (pulses with a duration of 1.5 µs) with a wavelength of 673 nm, versus the value of the light energy per second.
Figure 5:
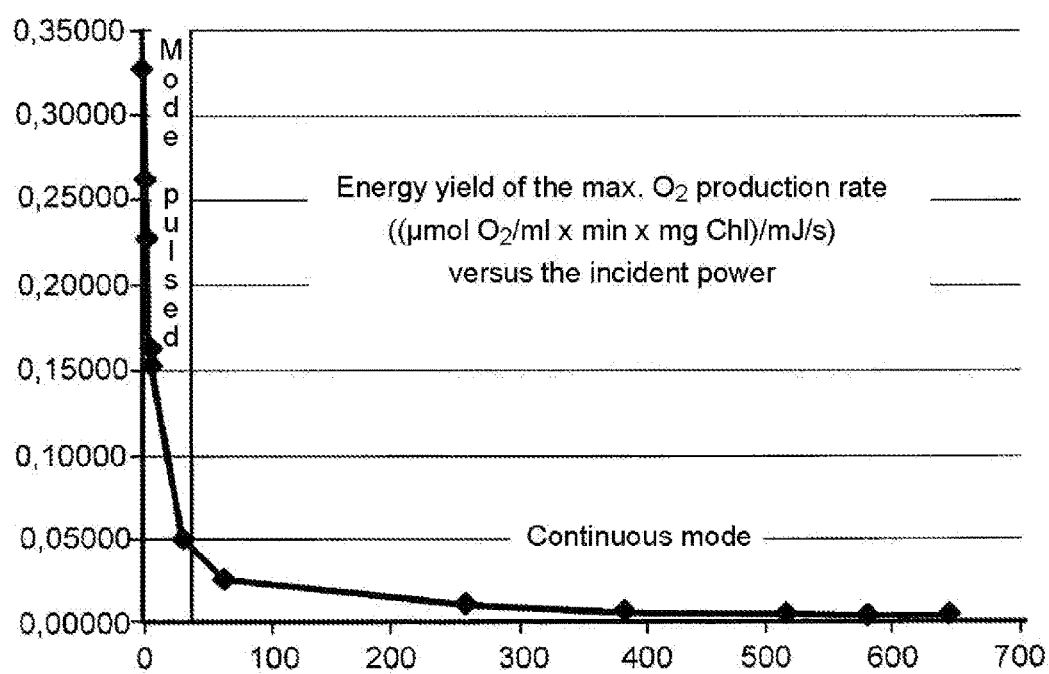
FIG. 5 illustrates the curves of the time-dependent change in the maximum energy yield of oxygen production rate obtained by the method in the presence of continuous coherent light, or pulsed coherent light at 800 Hz (pulses with a duration of 1.5 µs) with a wavelength of 673 nm, versus the value of the light energy per second.
Figure 6:
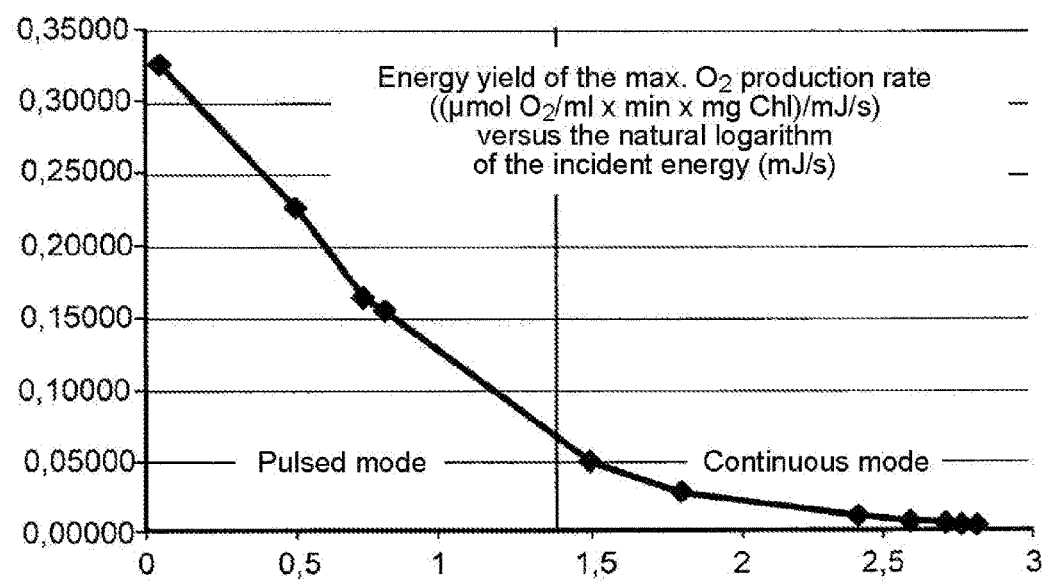
FIG. 6 illustrates the curves of the time-dependent change in the maximum energy yield of oxygen production obtained with the method in the presence of continuous coherent light, or of pulsed coherent light at 800 Hz (pulses with a duration of 1.5 µs), with a wavelength of 673 nm, depending on the value of the light energy per second (the energy being expressed in a logarithmic scale).

The analysis of FIGS. 4 to 6, and in particular of FIGS. 5 and 6, gives the possibility of demonstrating that the energy yield in pulsed mode is increased by a factor ranging from 1.03 to 61.75 according to the pulse frequency and therefore to the amount of energy per second, as compared with the application of the method in the presence of continuous light at an equal power.

The results of FIG. 5 are copied in the following Table 3:

TABLE 3

| Energy (mJ/s) | Energy yield K (O$_2$) μmoles/(25 μg Chl ml min)/mJ | Factor of increase in the yield ** |
|---|---|---|
| 1.10 | 0.32727 | 61.75 |
| 3.21 | 0.22804 | 43.03 |
| 5.50 | 0.16364 | 30.87 |
| 6.42 | 0.15576 | 29.39 |
| 32.10 | 0.04984 | 9.40 |
| 64.20 | 0.02741 | 5.17 |
| 256.80 | 0.01137 | 2.15 |
| 385.20 | 0.00779 | 1.47 |
| 513.60 | 0.00631 | 1.19 |
| 577.80 | 0.00547 | 1.03 |
| 642 | 0.00530 | 1.00 |

** as compared with continuous light at an energy of 642 mJ/s

It should be understood that the present disclosure is by no means limited to the embodiments described above and that many modifications may be brought thereto within the scope of the appended claims.

The present application may also reference quantities and numbers. Unless specifically stated, such quantities and numbers are not to be considered restrictive, but exemplary of the possible quantities or numbers associated with the present application. Also in this regard, the present application may use the term "plurality" to reference a quantity or number. In this regard, the term "plurality" is meant to be any number that is more than one, for example, two, three, four, five, etc. The terms "about," "approximately," "near," etc., mean plus or minus 5% of the stated value. For the purposes of the present disclosure, the phrase "at least one of A, B, and C," for example, means (A), (B), (C), (A and B), (A and C), (B and C), or (A, B, and C), including all further possible permutations when greater than three elements are listed.

The principles, representative embodiments, and modes of operation of the present disclosure have been described in the foregoing description. However, aspects of the present disclosure which are intended to be protected are not to be construed as limited to the particular embodiments disclosed. Further, the embodiments described herein are to be regarded as illustrative rather than restrictive. It will be appreciated that variations and changes may be made by others, and equivalents employed, without departing from the spirit of the present disclosure. Accordingly, it is expressly intended that all such variations, changes, and equivalents fall within the spirit and scope of the present disclosure, as claimed.

The invention claimed is:

1. A method for dissociating an aqueous solution, comprising:
   first electrochemical oxidating the aqueous solution in the presence of pulsed light, said pulsed light being generated from a first source of light energy at a predetermined pulse frequency value, and having a predetermined peak power, by an enzymatic composition based on a first enzymatic complex PSII, isolated from a second enzymatic complex PSI, with production of oxygen, free electrons and free protons in the aqueous solution, wherein said light energy from said first source of light energy has a variable energy value over time, said variable energy value over time having a light energy value per second determined over a plurality of pulses of said pulsed light;
   capturing said free electrons and of said free protons;
   capturing oxygen; and
   modulating said predetermined pulse frequency value of said pulsed light to a sufficient pulse frequency value in order to obtain a first oxygen production yield per unit of light energy which is greater by a factor (f) of 1.01 to 100.00 than a second oxygen production yield per unit of light energy obtained for a second electrochemical oxidation in the presence of continuous light,
   said first and second oxygen production yields ($\eta_i$) being each obtained from an oxygen production rate ($K(O_2)_i$) per unit of light energy, i=1 or 2, such that:

$$\eta_i = \frac{K(O_2)_i}{E_i},$$

where $E_i$ refers to an amount of energy per second provided for obtaining said oxygen production rate ($K(O_2)_i$), i=1 or 2, said factor (f) being equal to a ratio between said first oxygen production yield ($\eta_1$) and said second oxygen production yield ($\eta_2$) such that:

$$f = \frac{\eta_1}{\eta_2},$$

said pulsed light and said continuous light having an equal predetermined wavelength and said continuous light have an equal power to said predetermined peak power of said pulsed light.

2. The method according to claim 1, comprising, before said electrochemical oxidation of said aqueous solution, extracting said enzymatic complex PSII from chloroplasts or tylakoids of chloroplasts.

3. The method according to claim 2, comprising, after extracting said PSII, purifying said enzymatic complex PSII in order to form an enzymatic composition substantially concentrated in PSII.

4. The method according to claim 2, wherein said chloroplasts or tylakoids of chloroplasts are chloroplasts or tylakoids of chloroplasts of plants from the family of Chenopodiaceae.

5. The method according to claim 1, comprising, before said electrochemical oxidation of said aqueous solution, synthetically manufacturing said enzymatic complex PSII.

6. The method according to claim 1, wherein said capture of free electrons and of free protons is carried out by an electron transport mediator selected from the group consisting of derivatives of quinone, 2,6-dimethylbenzoquinone, 2,6-dichloro-p-benzoquinone and 1,4-benzoquinone, and one of their mixtures.

7. The method according to claim 1, wherein said pulsed light is emitted at a pulse frequency comprised between 1 Hz and 100 MHz, preferably comprised between 1 Hz and 3,000 Hz, in a range of wavelengths comprised between 400 nm and 700 nm, at a peak power comprised between 1 mW and 800 mW.

8. The method according to claim 1, wherein said oxidation of water is carried out at a pH comprised between 4 and 8.

9. The method according to claim 1, wherein said energy value is determined based on a plurality of pulses over a time interval of 1 s.

* * * * *